(12) United States Patent
Grant et al.

(10) Patent No.: US 10,754,665 B2
(45) Date of Patent: Aug. 25, 2020

(54) METHOD FOR CONFIGURING A MEDICAL IMAGING DEVICE, SYSTEM FOR CONFIGURING A MEDICAL IMAGING DEVICE, COMPUTER PROGRAM PRODUCT AND COMPUTER READABLE MEDIUM

(71) Applicant: Siemens Healthcare GmbH, Erlangen (DE)

(72) Inventors: Katharine Lynn Rowley Grant, Rochester, MN (US); Thomas Flohr, Uehlfeld (DE); Bernard Schmidt, Fuerth (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/033,327

(22) Filed: Jul. 12, 2018

(65) Prior Publication Data

US 2019/0026128 A1    Jan. 24, 2019

(30) Foreign Application Priority Data

Jul. 19, 2017 (EP) ..................... 17182083

(51) Int. Cl.
| | |
|---|---|
| *G06F 9/445* | (2018.01) |
| *G16H 40/63* | (2018.01) |
| *A61B 6/03* | (2006.01) |
| *A61B 6/00* | (2006.01) |

(52) U.S. Cl.
CPC .......... *G06F 9/44505* (2013.01); *A61B 6/032* (2013.01); *A61B 6/545* (2013.01); *A61B 6/547* (2013.01); *A61B 6/563* (2013.01); *G16H 40/63* (2018.01)

(58) Field of Classification Search
CPC ....... A61B 6/032; A61B 6/037; A61B 6/5205; A61B 6/035; A61B 5/0536; A61B 6/482; G01N 23/046; G01N 21/4795; G01N 2223/419; G06T 2207/10081; G06T 11/005; G06F 19/321; G06F 9/44505
USPC ................ 378/4, 62; 600/547, 425; 382/131
See application file for complete search history.

(56) References Cited

U.S. PATENT DOCUMENTS

| | | | | |
|---|---|---|---|---|
| 6,711,617 B1 * | 3/2004 | Bantz | .................. | H04L 41/0816 370/401 |
| 7,613,672 B2 * | 11/2009 | West | ...................... | G06F 19/00 706/48 |
| 7,668,286 B2 * | 2/2010 | Tsuyuki | ................. | A61B 6/032 378/16 |

(Continued)

OTHER PUBLICATIONS

European Summons to Attend Oral Proceedings dated May 13, 2019.

(Continued)

*Primary Examiner* — Faisal M Zaman
(74) *Attorney, Agent, or Firm* — Harness, Dickey & Pierce, P.L.C.

(57) ABSTRACT

A method is disclosed for configuring a medical imaging device. In at least one embodiment, the method includes providing an input data set specifying a clinical task, the input data set including quantified image requirements; transferring the input data set to a server; providing a configuration data set by the server depending on the input data set; transferring the configuration data set from the server to the medical imaging device within a defined time interval; and configuring the medical imaging device based on the configuration data set.

24 Claims, 1 Drawing Sheet

(56) References Cited

U.S. PATENT DOCUMENTS

| | | | |
|---|---|---|---|
| 8,000,510 B2 | 8/2011 | Boeing et al. | |
| 8,687,762 B2 | 4/2014 | Feuerlein et al. | |
| 9,615,804 B2* | 4/2017 | Scheuering | A61B 6/5294 |
| 9,636,077 B2 | 5/2017 | Braun et al. | |
| 2003/0092983 A1* | 5/2003 | Baker | A61B 6/032 |
| | | | 600/428 |
| 2004/0131141 A1* | 7/2004 | Horiuchi | A61B 6/542 |
| | | | 378/4 |
| 2005/0090742 A1* | 4/2005 | Mine | A61B 8/0833 |
| | | | 600/443 |
| 2007/0109294 A1 | 5/2007 | Ben-Tal | |
| 2008/0294458 A1 | 11/2008 | Skupin | |
| 2012/0014499 A1* | 1/2012 | Feuerlein | A61B 6/032 |
| | | | 378/5 |
| 2014/0233041 A1* | 8/2014 | Reitz | A61B 6/581 |
| | | | 356/614 |
| 2014/0270053 A1* | 9/2014 | Larson | A61B 6/032 |
| | | | 378/4 |
| 2015/0085066 A1* | 3/2015 | Desai | G16H 40/63 |
| | | | 348/14.08 |
| 2015/0199478 A1 | 7/2015 | Bhatia et al. | |
| 2016/0089103 A1* | 3/2016 | Darrow | A61B 5/055 |
| | | | 600/425 |
| 2016/0242727 A1* | 8/2016 | Flohr | A61B 6/032 |
| 2017/0000447 A1* | 1/2017 | Profio | A61B 6/545 |
| 2017/0124271 A1* | 5/2017 | Aase | G06F 19/00 |
| 2017/0209107 A1* | 7/2017 | Park | A61B 6/54 |
| 2017/0347988 A1* | 12/2017 | Liang | A61B 8/0841 |
| 2018/0128890 A1* | 5/2018 | Schor | G16H 40/63 |
| 2018/0228450 A1* | 8/2018 | Vega | A61B 6/5217 |
| 2018/0368731 A1* | 12/2018 | Oh | G06T 7/0016 |

OTHER PUBLICATIONS

Kypro H. Nicolaides : "The 11 to 13 +6 weeks scan", Dec. 31, 2004 (Dec. 31, 2004), XP055515782; Retrieved from the Internet: URL:http://www.fetalmedicine.com/fmf/FMF-English.pdf; 2004.

European Office Action dated Oct. 29, 2018.

Result of Consultation issued Jan. 29, 2020 in European Application No. 17 182 083.0.

Decision to Refuse a European Patent Application dated Mar. 30, 2020 in European Application No. 17 182 083.0.

* cited by examiner

METHOD FOR CONFIGURING A MEDICAL IMAGING DEVICE, SYSTEM FOR CONFIGURING A MEDICAL IMAGING DEVICE, COMPUTER PROGRAM PRODUCT AND COMPUTER READABLE MEDIUM

PRIORITY STATEMENT

The present application hereby claims priority under 35 U.S.C. § 119 to European patent application number EP17182083.0 filed Jul. 19, 2017, the entire contents of which are hereby incorporated herein by reference.

FIELD

At least one embodiment of the present invention describes a method for configuring a medical imaging device, a system for configuring a medical imaging device, a computer program product and a computer readable medium.

BACKGROUND

Medical instruments such as medical imaging devices are well known in the state of the art. These medical imaging devices have to be configured properly by a clinician for each usage and adapted to the specific task for achieving a desired result. Usually, medical instruments offer many configuration options that can be adapted for performing the specific medical task in the best way. Typically, these parameters depend on each other in a complex manner such that the proper configuration of the medical instruments strongly depends on the experience of the user.

U.S. Pat. No. 8,000,510 B2 discloses a method to control a slice image acquisition system, wherein a scan protocol is initially selected from a number of scan protocols and an automatic control of the slice image acquisition system ensues on the basis of the selected scan protocol.

U.S. Pat. No. 8,687,762 B2 discloses a CT system for scanning a patient, comprising a computer system to control the CT system, the computer system including an evaluation unit for a logical decision tree to determine examination and scan parameters for the CT system.

U.S. Pat. No. 9,615,804 B2 discloses a method for generating a medical image and evaluating the medical image, wherein the image data are evaluated by a given analysis application and a secondary application automatically proposes a set of parameter values coordinated to the given analysis application and/or given patient information.

U.S. Pat. No. 9,636,077 B2 discloses a method for an automatic selection of a scanning protocol for a tomographic recording of an X-ray image of a patient, the method comprising automatically comparing a patient-specific value with retrievably stored reference values, wherein one scanning protocol can be associated with each reference value.

U.S. Pat. No. 2,008,029 4458 A1 discloses a device for controlling and/or monitoring at least one apparatus during a medical intervention, wherein the device includes at least one control unit for controlling and/or monitoring the at least one apparatus.

US 2017 0124271 A1 relates to a method and a system for providing a social network to facilitate user sharing, distributing, ranking, and searching medical device configuration items.

US 2015 0 199 478 A1 relates to a system and a method for identifying image acquisition parameters.

For example, the medical imaging device is a computer tomography (CT)-scanner. In the case of patients with chest pain, one can choose
- a single low energy kV scan (e. g. 70/80 kV) of a thorax at a low pitch for ac-cumulating a sufficient radiation dose due to a limitation of a x-ray tube at low kV or
- a medium energy kV scan (e. g. 100 kV) at a high pitch.

Additionally, CT scans can be performed in a dual or single energy mode as well as with or without an ECG-gating. Similar variances are possible with regard to the application of iodinated contrast media. For example, either a short injection at a high contrast injection rate or a longer injection at a lower injection rate can be selected.

Furthermore, to optimize image quality, e. g. in terms of motion artifacts, and maintain a clinically desired radiation dose level, one can either reduce the pitch at a faster gantry rotation or keep the pitch high at a slower gantry rotation. Smaller detector collimations might provide better images due to less scatter and cone beam artifacts but require longer scan times as well as a longer contrast media injection and a more challenging scan timing. Similar issues are seen on the reconstruction side. Depending on the clinical task and the preference of the user, images at different slice width can be reconstructed or quantitative of edge enhancing reconstruction kernels can be used.

SUMMARY

At least one embodiment of the present invention provides a method for supporting a user by choosing the proper configuration of a medical imaging device, in particular a medical imaging device.

At least one embodiment is directed a method for configuring a medical imaging device. At least one embodiment is directed to a system. At least one embodiment is directed to a computer program product. And at least one embodiment is directed to a computer readable computer medium.

According to a first embodiment of the present invention, a method for configuring a medical imaging device, is provided, comprising:
- providing an input data set specifying a clinical task;
- transferring the input data set to a server;
- providing a configuration data set depending on the input data by the server;
- transferring the configuration data set from the server to the medical imaging device within a defined time interval, in particular real-time; and
- configuring the medical imaging device based on the configuration data set, in particular configuring a recording setting and/or reconstruction setting of the medical imaging device.

According to another embodiment of the present invention, a system for configuring a medical imaging device comprising the medical imaging device and a server is provided, wherein the system is configured for:
- providing an input data set specifying a clinical task;
- transferring the input data set to a server;
- providing a configuration data set by the server depending on the input data set;
- transferring the configuration data set from the server to the medical imaging device within a defined time interval; and
- configuring the medical imaging device based on the configuration data set, in particular configuring a recording setting and/or reconstruction setting of the medical imaging device.

Another embodiment of the present invention is directed to a computer program product for carrying out the steps of the method according to at least one embodiment of the present invention when the computer program product is loaded into a memory of a programmable device.

A further embodiment of the present invention is a computer-readable medium on which is stored a program elements that can be read and executed by a computer unit in order to perform steps of the method according to at least one embodiment of the present invention when the program elements are executed by the computer unit.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the FIGURES. It will be understood that the spatially relative terms are intended to encompass different orientations of the device in use or operation in addition to the orientation depicted in the FIGURES. For example, if the device in the FIGURES is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the FIGURES. For example, two FIGURES shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the FIGURE. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

According to a first embodiment of the present invention, a method for configuring a medical imaging device, is provided, comprising:
 providing an input data set specifying a clinical task;
 transferring the input data set to a server;
 providing a configuration data set depending on the input data by the server;
 transferring the configuration data set from the server to the medical imaging device within a defined time interval, in particular real-time; and
 configuring the medical imaging device based on the configuration data set, in particular configuring a recording setting and/or reconstruction setting of the medical imaging device.

In at least one embodiment a server, in particular a protocol server, is used for providing a configuration data set that can be selected by the user, in particular a clinician, for configuring the medical imaging device, for example for setting a scan protocol and/or reconstruction settings of a CT scanner. Preferably, the configuration data set comprises a recommended set of configuration parameters and especially the configuration parameters are based on the respective input data set. Thereby, the server relies on data being available to the server such as an updated data base that comprises a comparatively high number of configuration data sets or configuration parameters, which were used for similar starting conditions in the past.

Furthermore, in at least one embodiment the server can establish a link between correlated configuration parameter that might be not obvious to the user. Preferably, the configuration data set is transferred to the medical imaging device in real time. Thus, the user can immediately use the configuration data set adapted to the present case for configuring the medical imaging device. In particular, the medical imaging device comprises a transmitter for transferring the input data set to the server and a receiver for receiving the configuration data set from the server.

Furthermore, in at least one embodiment the server comprises a processor configured for providing or for recommending a configuration data set based on the input data set. In particular, it is provided that the server is updated. Thus, the configuration data sets are based on criteria being regularly or constantly updated.

The term "input data set" preferably describes such data comprising information about a clinical task and/or a clinical request that should be performed by the medical imaging device. According to at least one embodiment of the present invention the input data set includes quantified image requirements such a specific image noise, a sharpness of an edge function and/or an acceptable radiation dose. It is also thinkable that the input data set includes preferences of the user regarding specific configuration parameter. Preferably, information concerning the input data set is entered to the medical imaging device by using an input device and/or the input data set is transmitted to the server automatically. Furthermore, the medical imaging device is configured for displaying the configuration data set, for example on a screen of a workstation, a tablet and/or a smartphone. Preferably, the medical imaging device is a CT-scanner. In particular, the server is a network or a part of a network.

Particularly advantageous embodiments and features of the invention are given by the claims as revealed in the following description. Features of different claim categories may be combined as appropriate to give further embodiments not described herein.

According to a example embodiment it is provided that the input data set comprises patient information, a medical indication and/or information concerning the medical imaging device. Preferably, the patient information describes the patient appropriately, for example by weight, size, shape, vector with attenuation values and/or laboratory data. The information concerning the medical imaging device might comprise a type designation, a version designation of the medical imaging device and/or a present configuration of the medical imaging device. Thus, it is advantageously possible to optimize the configuration parameter for the present case by taking into account information about the patient as well as the information about the specific medical imaging device. In other words: it is possible to configure the medical imaging device individually for the present case.

In a further example embodiment of the present invention, it is provided that the configuration data set is used for automatically configuring the medical imaging device. For example, the user can select the configuration data set being recommended by the server and preferably at least a subset of the configuration parameters is automatically set by the medical imaging device, for example in the subsequent scanning and/or reconstruction process.

Preferably, it is provided that a preference data set including a preselection of one or several configuration parameters is transferred to the server. The preference data set preferably comprises a subset of configuration parameters that are preferred by the user. In particular, the preference data set suggests changes of specific parameter of the recommended configuration data set. For example the user prefers a scan time being shorter than the scan time being suggested by the configuration data set. Preferably, the preference data set is transferred to the server after transferring the configuration data set from the server to the medical imaging device. Thus, the user can incorporate into the preference data set information or preferred parameter when he disagrees with a specific parameter recommended in the configuration data set.

In another example embodiment, it is provided that a further configuration data set depending on the input data set and the preference data set are provided by the server, wherein the further configuration data set is transferred to the medical imaging device. In contrast to the configuration data set being suggested by the server in the first place the further configuration data set includes the preferred configuration parameters of the user or configuration parameters as close as possible to the preferred configuration parameters. Thus, the configuration parameters be-sides the preferred configuration parameters of the user can be adapted by the server, preferable by taking into account the input data set and the preferred con-figuration parameter of the user.

According to another example embodiment, it is provided that a plurality of con-figuration data sets depending on the input data by the server are provided and transferred from the server to the medical imaging device. Thereby the user can advantageously choose between different configuration data sets and select one of the recommended configuration data sets for configuring the medical imaging device. In particular, a plurality of alternative configuration data sets is provided by the server. As a consequence, the user can choose that configuration data set that the user prefers.

In at least one example embodiment, it is provided that additional information classifying the respective configuration data set is added to each configuration data set of the plurality of configuration data sets. The additional information advantageously supports the user by choosing one of the several configuration data sets. For example, the additional information presents a scanning time or a radiation dose for each of the alternative configuration data sets. Thus, the user can compare the additional information for the respective alternative configuration data sets and make a decision based on this comparison.

In at least one example embodiment, it is provided that the provided configuration data set is further based on a feedback data set including a rating of a previous configuration data set and/or a location of the medical imaging device. By providing the configuration data set based on a previous feedback it is possible to avoid using a suboptimal configuration data set again. By providing the configuration data set based on the location it is advantageously possible to take specific dose limits into account, such country specific dose limits or a dose limit associated to a clinic department.

In another example embodiment, it is provided that the medical imaging device is informed about an abnormality in the input data set. This abnormality might be an indication of a misalignment of the medical imaging device. Thus, the user can use the information about the abnormality and initiate countermeasures.

According to an example embodiment, the server is trained by the input data sets. Thus, the quality of recommend configuration data sets can be further improved. For example, the trained server discovers a correlation between the input data and the configuration data sets and uses the correlation for recommending the configuration data set.

In at least one example embodiment, a machine learning mechanism is used for training the server. In particular, input data sets are incorporated to the server, when no feedback or a positive feedback is given by the user. As a consequence, the selection criteria for providing the configuration data set are refined constantly. For gaining know-how the server is preferably supplied with information regarding the radiation dose, the objective image quality and/or protocol specific contrast injection parameter in addition. In particular, the information is decoupled from the Digital Imaging and Communications in Medicine (DICOM). Thus, just the information can be transferred without DICOM data submission.

In particular, it is provided that parameters of the input data set are determined by the server. Thus, only the necessary parameters are included into the input data set.

According to another embodiment of the present invention, a system for configuring a medical imaging device comprising the medical imaging device and a server is provided, wherein the system is configured for:
   providing an input data set specifying a clinical task;
     transferring the input data set to a server;
      providing a configuration data set by the server depending on the input data set;

transferring the configuration data set from the server to the medical imaging device within a defined time interval; and configuring the medical imaging device based on the configuration data set, in particular configuring a recording setting and/or reconstruction setting of the medical imaging device.

Another embodiment of the present invention is directed to a computer program product for carrying out the steps of the method according to at least one embodiment of the present invention when the computer program product is loaded into a memory of a programmable device.

A further embodiment of the present invention is a computer-readable medium on which is stored a program elements that can be read and executed by a computer unit in order to perform steps of the method according to at least one embodiment of the present invention when the program elements are executed by the computer unit.

Figure 1:
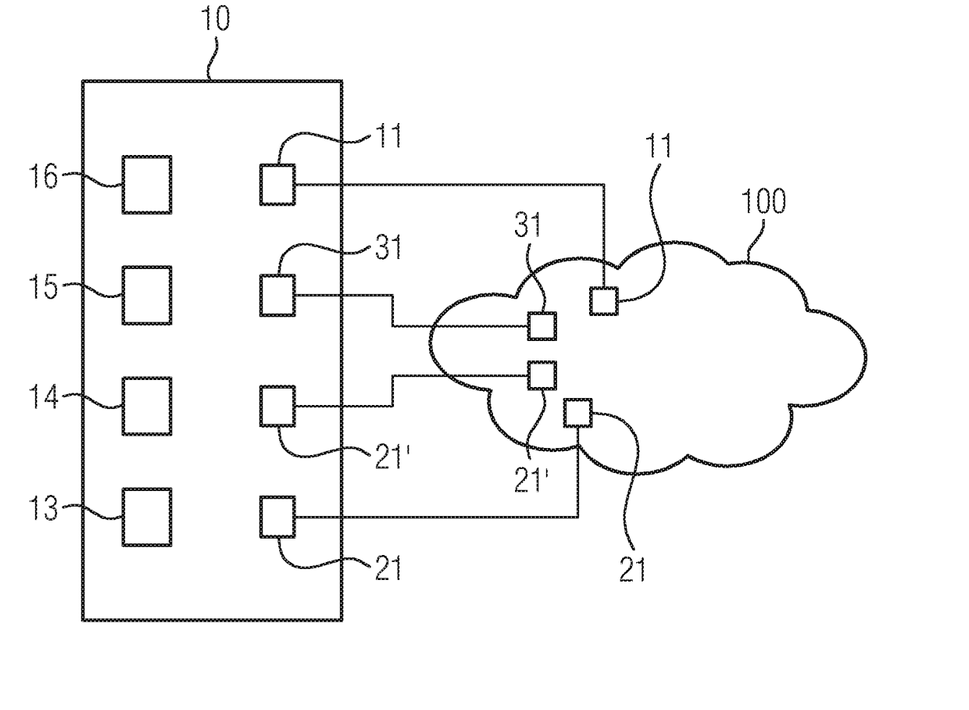
FIG. 1 shows schematically a method for configuring a medical imaging device according to an example embodiment of the present invention.

In FIG. 1 schematically a method for configuring a medical imaging device 10 according to an example embodiment of the present invention is illustrated. Preferably, the medical imaging device 10 is a CT-scanner. Those instruments offer many configuration options, in particular configuration parameters, to a user for setting the medical imaging device 10 in a mode that leads to the desired result. For example, the configuration parameters have to be individually adapted to each specific medical imaging device 10, to a configuration of the medical imaging device 10 and to a patient for achieving the best result that is possible be using the imaging device 10. Thereby, the output, in particular a quality of the output, strongly depends on an experience of the user for using the specific medical imaging device 10.

In order to support the user it is provided, that in a beginning an input data set 11 is provided, preferably automatically by the medical imaging device 10. Such an input data set 11 comprises patient information and/or information concerning the medical imaging device, such as a kind of medical imaging devices 10 and/or its configuration. Information concerning the medical imaging device might be performance values and/or consumption values of the medical imaging device over a previous period of time. For example, the patient information is a weight, a size, a shape, a vector with attenuation values and/or laboratory data. This patient information might be entered to the medical imaging device 10 by an input device 15. Furthermore, it is provided, that the input data set 11 comprises a clinical task and/or clinical request.

Preferably, it is provided that the medical imaging device 10 collects automatically the information for compiling the input data set 11. In particular, the medical imaging device 10 has a processor unit 14 being configured for collecting the information and providing the input data set 11. After compiling the input data set 11 it is provided that the input data set 11 is transferred to a server 100. The server 100 is configured such that a configuration data set 21 is provided based on the input data set 11. For example, the configuration data set 21 comprises configuration parameters used for scanning and/or reconstruction of an image data set recorded by a medical imaging device such as a CT scanner. Thereby it is possible that the server 100 can rely on the experience of the server, in particular on the amount of data being available to the server 100. Another advantage is that such a sever 100 can be updated permanently. Therefore, the suggested configuration data set 100 is based on the latest developments concerning the adapting of the medical imaging devices 10.

Subsequently, the suggested configuration data 21 set is transferred to the medical imaging device 10. For instance, the suggested configuration data set 21 is presented on a display 13, for example on a screen of a workstation, a tablet or a smartphone. Following up the displaying the user preferable chooses whether he wants to use the configuration parameters of the configuration data set 21 suggested by the server. In the case the user agrees with the configuration parameter he can select, preferably by using the input device 15, the configuration data set 21 and the medical imaging device 10 is configured based on the configuration parameters of the configuration data set 21.

It is also thinkable that the user does not agree with one or several configuration parameters of the configuration data set 21 and he wants to use instead preferred configuration parameters. Therefore, it is preferably provided that a preference data set 31 comprising for example the preferred configuration parameters is transferred to the server 100. As a consequence, the server 100 provides a further configuration data set 21' based on the input data set 11 and the preference data set 31. Preferably, the preference data set 31 comprises the preferred parameters and further parameters being adapted based on the preferred parameters and the input data set 11.

According to another embodiment, it is provided that the provided configuration data set 21 is additionally based on a previous feedback and/or a location of the medical imaging device 10. For example, in the past a configuration data set 21 recommended by the server led 10 to an insufficient result and the user gives a corresponding feedback to the server 100, for example by transferring a feedback data set to the server. As a consequence, the server 100 can take into account the feedback data set and suggest another configuration data set 21 next time. Furthermore, the input data set 11 further includes a location of the medical imaging device 10. As a consequence, the server can take into account for example specific dose limits that are assigned to this location. The term location preferably includes a specific environment of the medical imaging device. For example, the medical imaging device 10 can be located in a paediatric clinic, an oncological clinic or a screening clinic.

Preferably, it is provided that the medical imaging device 10 is informed about an ab-normality in the input data set 11. Thus, the user is additionally informed about abnormalities for example in the current configuration of the medical imaging device 10.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for configuring a computed tomography scanner, the method comprising:
   providing an input data set specifying a clinical task, the input data set including quantified image requirements;
   transferring the input data set to a server;
   providing, by the server, a plurality of configuration data sets based on the input data set and a specific environment of the computed tomography scanner;
   transferring the plurality of configuration data sets from the server to the computed tomography scanner within a defined time interval; and
   configuring the computed tomography scanner based on a selected configuration data set from among the plurality of configuration data sets, wherein
      additional information classifying each respective configuration data set among the plurality of configuration data sets is added to each respective configuration data set among the plurality of configuration data sets.

2. The method of claim 1, wherein the input data set further includes at least one of patient information, a medical indication or information concerning the computed tomography scanner.

3. The method of claim 1, wherein the selected configuration data set is used for automatically configuring the computed tomography scanner.

4. The method of claim 1, further comprising:
   transferring a preference data set, including a selection of one or more configuration parameters, to the server.

5. The method of claim 4, further comprising:
   providing, by the server, a further configuration data set, the further configuration data set based on the input data set and the preference data set; and
   transferring the further configuration data set to the computed tomography scanner.

6. The method of claim 1, wherein
   the plurality of configuration data sets are further based on a feedback data set including a rating of a previous configuration data set; and
   the specific environment of the computed tomography scanner includes a location of the computed tomography scanner.

7. The method of claim 1, wherein the computed tomography scanner is informed about an abnormality in the input data set.

8. The method of claim 1, wherein the server is trained at least partly by the input data set.

9. The method of claim 8, wherein a machine learning mechanism is used for training the server.

10. The method of claim 1, wherein parameters of the input data set are determined by the server.

11. A system for configuring a computed tomography scanner, the system comprising:
   the computed tomography scanner; and
   a server, wherein the system is configured to
      provide an input data set specifying a clinical task, the input data set including quantified image requirements,
      transfer the input data set to the server,
      provide, by the server, a plurality of configuration data sets based on the input data set and a specific environment of the computed tomography scanner,
      transfer the plurality of configuration data sets from the server to the computed tomography scanner within a defined time interval, and
      configure the computed tomography scanner based on a selected configuration data set from among the plurality of configuration data sets, wherein
         additional information classifying each respective configuration data set among the plurality of configuration data sets is added to each respective configuration data set among the plurality of configuration data sets.

12. A non-transitory computer program product including program elements for carrying out the method of claim 1 when the non-transitory computer program product is loaded into a memory of a programmable device.

13. A non-transitory computer-readable medium, storing program elements readable and executable by a computer unit, to perform the method of claim 1 when the program elements are executed by the computer unit.

14. The method of claim 1, wherein the configuring the computed tomography scanner includes configuring at least one of a recording setting or a reconstruction setting of the computed tomography scanner.

15. The method of claim 2, wherein the selected configuration data set is used for automatically configuring the computed tomography scanner.

16. The method of claim 2, further comprising:
   transferring a preference data set, including a selection of one or more configuration parameters, to the server.

17. The method of claim 16, further comprising:
   providing, by the server, a further configuration data set, the further configuration data set based on the input data set and the preference data set; and
   transferring the further configuration data set to the computed tomography scanner.

18. The method of claim 3, further comprising:
   transferring a preference data set, including a selection of one or more configuration parameters, to the server.

19. The method of claim 18, further comprising:
   providing, by the server, a further configuration data set, the further configuration data set based on the input data set and the preference data set; and
   transferring the further configuration data set to the computed tomography scanner.

20. The method of claim 2, wherein
   the plurality of configuration data sets are further based on a feedback data set including a rating of a previous configuration data set; and
   the specific environment of the computed tomography scanner includes a location of the computed tomography scanner.

21. The method of claim 2, wherein the computed tomography scanner is informed about an abnormality in the input data set.

22. The system of claim 11, wherein the configuring the computed tomography scanner includes configuring at least one of a recording setting or a reconstruction setting of the computed tomography scanner.

23. The system of claim 11, wherein the input data set further includes at least one of patient information, a medical indication or information concerning the computed tomography scanner.

24. A non-transitory computer-readable medium, storing program elements readable and executable by a computer unit, to perform the method of claim 2 when the program elements are executed by the computer unit.

* * * * *

UNITED STATES PATENT AND TRADEMARK OFFICE
CERTIFICATE OF CORRECTION

PATENT NO. : 10,754,665 B2  
APPLICATION NO. : 16/033327  
DATED : August 25, 2020  
INVENTOR(S) : Katharine Lynn Rowley Grant et al.

Page 1 of 1

It is certified that error appears in the above-identified patent and that said Letters Patent is hereby corrected as shown below:

On the Title Page

At item (72):  
Bernard Schmidt, Fuerth (DE) should read -- Bernhard Schmidt, Fuerth (DE) --

Signed and Sealed this  
First Day of December, 2020

Andrei Iancu  
*Director of the United States Patent and Trademark Office*